United States Patent
Lima et al.

(10) Patent No.: US 11,179,297 B2
(45) Date of Patent: Nov. 23, 2021

(54) ANTIMICROBIAL POLYMERIC COMPOSITIONS CONTAINING METAL CONTAINING METHACRYLATES

(71) Applicant: UNIVERSIDADE FEDERAL DE PELOTAS, Pelotas (BR)

(72) Inventors: Giana da Silveira Lima, Pelotas (BR); Rafael Guerra Lund, Pelotas (BR); Evandro Piva, Pelotas (BR); Adriana Fernandes da Silva, Pelotas (BR); Wellington Luiz de Oliveira da Rosa, Pelotas (BR); Raissa Coi de Araújo, Pelotas (BR); Andressa Goicochea Moreira, Pelotas (BR); Julia Adornes Gallas, Pirassununga (BR); Tharsis Christini de Almeida Rossato, Rio Grande (BR); Juliana Silva Ribeiro, Pelotas (BR); Alexandra Rubin Cocco, Pelotas (BR); Sonia Luque Peralta, Fortaleza (BR)

(73) Assignee: UNIVERSIDADE FEDERAL DE PELOTAS, Pelotas (BR)

(*) Notice: Subject to any disclaimer, the term of this patent is extended or adjusted under 35 U.S.C. 154(b) by 78 days.

(21) Appl. No.: 15/656,731

(22) Filed: Jul. 21, 2017

(65) Prior Publication Data
US 2018/0021225 A1 Jan. 25, 2018

(30) Foreign Application Priority Data

Jul. 21, 2016 (BR) .......................... 1020160168830

(51) Int. Cl.
*A61K 6/889* (2020.01)
*A61K 6/16* (2020.01)
(Continued)

(52) U.S. Cl.
CPC ................ *A61K 6/889* (2020.01); *A61K 6/16* (2020.01); *A61K 6/25* (2020.01); *A61K 6/62* (2020.01);
(Continued)

(58) Field of Classification Search
CPC . A61K 6/889; A61K 6/16; A61K 6/25; A61K 6/62; A61K 6/69; A61K 6/70;
(Continued)

(56) References Cited

U.S. PATENT DOCUMENTS

2010/0068678 A1* 3/2010 Tanaka ................. A61K 6/0038
433/224
2013/0274426 A1* 10/2013 Sugiura .................... A61K 6/00
526/123.1

OTHER PUBLICATIONS

Yoshida et al., Color change capacity of dental resin mixed with silver methacrylate caused by light irradiation and heating, 2009, Dental Materials Journal, 28(3), 324-337. (Year: 2009).*

* cited by examiner

Primary Examiner — Trevor Love
(74) Attorney, Agent, or Firm — B. Aaron Schulman, Esq.; Stites & Harbison, PLLC

(57) ABSTRACT

Metal-containing methacrylates incorporated into polymeric materials with antimicrobial capacity for biomedical applications, and more particularly for dental purposes, are provided. The incorporation of metal-containing methacrylates such as calcium methacrylate, tin methacrylate, copper methacrylate, silver methacrylate, in combination or alone, for potentializing antimicrobial effect of cements, in particular, to biomaterial compositions including metal containing methacrylates, such as calcium, tin, copper, silver, nickel, titanium and iron methacrylates, in the formulation of biomaterials for applications in human health provides advantages, particularly in dentistry, and allows for expres-
(Continued)

sive antimicrobial activity to dental compositions, so as to be useful in dental prosthesis, operative dentistry, orthodontics, pediatric dentistry, implantodontics, and endodontics.

11 Claims, 2 Drawing Sheets

(51) Int. Cl.
*A61K 6/25* (2020.01)
*A61K 6/62* (2020.01)
*A61K 6/69* (2020.01)
*A61K 6/70* (2020.01)
*A61K 6/76* (2020.01)
*A61K 6/891* (2020.01)

(52) U.S. Cl.
CPC .................. *A61K 6/69* (2020.01); *A61K 6/70* (2020.01); *A61K 6/76* (2020.01); *A61K 6/891* (2020.01)

(58) Field of Classification Search
CPC . A61K 6/76; A61K 6/891; A61K 6/75; A61K 6/833; A61K 6/838; A61K 6/887
See application file for complete search history.

ANTIMICROBIAL POLYMERIC COMPOSITIONS CONTAINING METAL CONTAINING METHACRYLATES

FIELD OF THE INVENTION

The present invention relates, in particular, to biomaterials compositions including metal containing methacrylates, such as calcium, tin, copper, silver, nickel, titanium and iron methacrylates, in the formulation of biomaterials: for example, adhesive systems, sealants, cements, compomers and composites, among others. The compositions present varied applications in human health in special for dentistry providing expressive antimicrobial activity to dental compositions, such as in dental prosthesis, operative dentistry, orthodontics, pediatric dentistry, implantodontics, and endodontics.

BACKGROUND OF THE INVENTION

Antibacterial polymeric materials can be used in dentistry in areas such as dental prosthesis, operative dentistry, orthodontics, pediatric dentistry, dental implantology, endodontics.

Composites for Orthodontics Purpose

Polymeric materials, such as adhesive systems and resin cements, can be used for bonding orthodontic accessories. Self-etch adhesive resin cements are simplified materials that promote less damage to the dental structure, since they do not need the acid etching step before adhesive system application. They can either be indicated for cementing the fittings, or not. During orthodontic treatment, there is a transient change in the oral cavity during the period of time the orthodontic devices, such as brackets and bands, remain in the mouth; a situation that may promote an increasing risk of caries, as a result of factors related to dental biofilm retention. Thus, antimicrobial agents in orthodontic materials could prevent or reduce the chances of developing caries lesions (GORELICK; GEIGER; GWINNETT, 1982).

Some antimicrobial agents, such as particles or substances may be incorporated into these materials, however they may be leached into the oral cavity and lost over time, exerting a primarily transient effect. Studies have reported the use of benzalkonium chloride (ALTHEM et al., 2006), Cetylpyridinium chloride (AL-MUSALLAM et al., 2006), silver particles (AHN et al., 2009), chlorhexidine (CACCIAFESTA et al., 2006) and triclosan (SEHGAL et al., 2007) as antimicrobial agents. Other potential antibacterial additives are listed in study of Cocco et al., 2015.

On the other hand, the advantage of adding antimicrobial metal containing methacrylates monomers is that they can be incorporated into the resin matrix, constituting a polymer, so by this way antimicrobial additives are not transient, but will act in the long term due to crosslinking of metal-containing methacrylates after polymerization, resulting in a very low quantity of leachable residual monomers. Recent studies have evaluated the incorporation of zinc methacrylate into experimental adhesive systems (Henn et al., 2011; Henn et al., 2012) and have shown promising results of antimicrobial action against Streptococcus mutans, the main cause of caries disease—commonly occurring in patients undergoing orthodontic treatment (GORELICK; GEIGER; GWINNETT, 1982.

The patent WO2011123915 (2012) describes a method for preparing an aqueous antimicrobial solution containing chlorhexidine and tartaric acid for use with an orthodontic glass ionomer cement. US 20070172434 A1 (2006) relates to compositions and methods for materials such as cements and orthodontic devices, however, at the best of the knowledge, the use of metal containing monomers and antimicrobial groups in the composition has not yet been claimed. While EP1749514 (2002) comprises a dental composition with a silver and zinc zeolite, containing at least one monomer that has an ethylenically unsaturated group, and a polymerization initiator system. Although it may possibly have antimicrobial effect, the use of metal-containing methacrylates is not claimed in the composition.

Once the bracket has been removed, a layer of residual resin remains adhered on the tooth enamel surface. In this context, the use of an antimicrobial cementing agent and contrasting or different staining of the tooth structure seems to be an interesting alternative to the bonding agents commonly used. In addition, this contrast helps the correct positioning of the brackets and identification for removal of possible excess material which, if not removed, can generate bacterial plaque accumulation and consequent susceptibility to caries lesions. Differential staining may be achieved with the development of new colored materials, for example by using the metal-containing methacrylates that may confer color change along with the antimicrobial effect. BRPI0702112A2 (2007) discloses the use of colored resin (containing artificial or natural dyes in the composition) for bonding orthodontic accessories. In the meantime, U.S. Pat. No. 6,379,593 B1 (1998) provides a method for producing a multi-colored portion to perform(?) a dental restoration, and a device for carrying out the process, such as by the CAD-CAM method. However, both patents do not envisage the use of metal-containing methacrylates as colorants in the composition.

Polymer Materials in Endodontics

In the area of endodontics, complete root canal system filling is a key factor for successful endodontic therapy. The main reason for this is that even after biomechanical preparation, the root canal walls may contain microorganisms capable of irritating the periapical tissues (NGUYEN, 2007; PÉCORA, 2010; SOUZA-NETO, 2011). Marginal microleakage may also contribute to recontamination of the root canal.

To prevent the invasion of microorganisms and fluid penetration, the endodontic cement should adhere firmly to dentin and gutta-percha. This seal would eliminate fluid penetration and would make the filling more resistant to displacement in the subsequent manipulations (GOGOS et al., 2003). The following list indicates a series of characteristics that the root canal filling should have: 1) it should not be a putrefying agent; 2) must have permanent antiseptic qualities; 3) should be easy to introduce into the root canal system; 4) must be biocompatible; 5) should not discolor the dental structures; 6) should not be porous and should remain dimensionally stable; 7) should be easy to remove from the inside of the channel if necessary; 8) should hermetically seal the dentinal tubules and apical foramen against bacterial invasion; 9) must be radiopaque; 10) must have good bond to the root canal walls; 11) should have a satisfactory consistency (PRINZ, 1912; FISHER, 1927; PUTERBAUGH, 1928; GROSSMAN, 1958; FRAUNHOFER; BRANSTETTER, 1982).

U.S. Pat. Nos. 6,197,846B1 (1998), 4,657,592A (1987), CA2334687A1 (1998) report the use of endodontic sealers containing antimicrobial agents in their composition, but they have no metal-containing methacrylates in them. No material available on the market at present, has all the characteristics of an ideal material. The differential of the technology being described in this article is the unprecedented incorporation of metal-containing methacrylates into dental polymer compositions, whose antimicrobial effect will help to preserve the dental tissue. Moreover, metal-containing methacrylates can also alter the characteristics and properties of the material to which they are added, according to its composition, thereby favoring its performance of the respective clinical application.

SUMMARY OF THE INVENTION

The present invention seeks to provide novel use of metal-containing methacrylates incorporated into polymeric dental materials. The present invention also seeks to provide materials with antimicrobial capacity for biomedical applications, and more particularly for dental purposes. The incorporation of metal-containing methacrylates such as calcium methacrylate, tin methacrylate, copper methacrylate, silver methacrylate—together or alone—potentiates the antimicrobial effect of the cements.

DETAILED DESCRIPTION OF THE INVENTION

Figure 1:
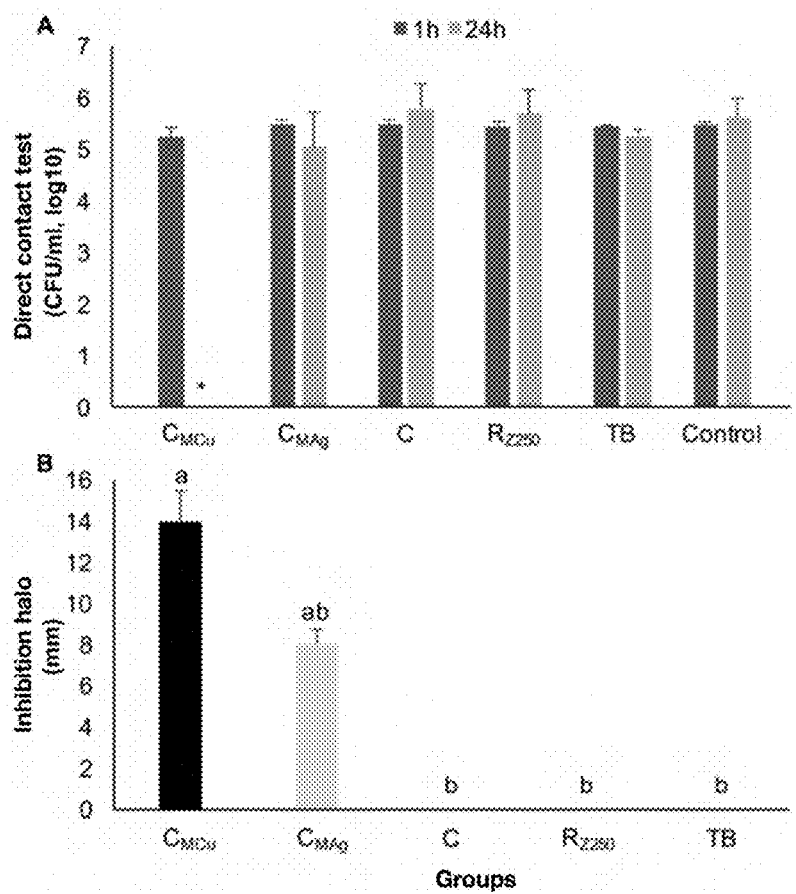
FIG. 1 shows Direct Contact (A) and Inhibition Halo Test (B) of orthodontic cements. *Only MCMC showed no bacterial growth in the direct contact assay (A). Different letters indicate statistical differences between groups (B) ($p<0.05$).

The present invention relates to dental compositions with the incorporation of metal-containing methacrylates in order to provide antimicrobial effects for dental material compositions such as cements, adhesives, resins, sealants, restorative materials, among others.

Metal-Containing Methacrylates

Metal-containing Methacrylates which may be used in polymer compositions or resin modified glass ionomer cements include calcium methacrylate, tin methacrylate, copper methacrylate, silver methacrylate, nickel methacrylate, zinc methacrylate, titanium methacrylate, iron methacrylate.

Forms of Presentation

Preferably, the material is composed of one component, which may be self-activating, photoactivated, chemically activated or dual cured. Moreover, the material is composed of two components in the form of two pastes. Alternatively, it is possible to present the product: a) in the form of powder and liquid; and b) as a single paste already containing the metal-containing methacrylates. Methacrylates may be encapsulated in a delivery system (such as microspheres, nanotubes, bioactive glass beads) so that after the structure is disrupted, the monomers may be released. Disruption may also occur through the reaction between two or more pastes. Furthermore, the presentation as "powder and paste" or "liquid and paste" can be used, so that the methacrylates in the form of powder or solution are incorporated into the paste containing the material at the time of application. As yet another alternative, the material may be presented in the form of an aqueous solution, such as for use in intracanal medications; for this application, the methacrylates may already be incorporated into the medication solution, or they may be mixed with it at the time of use.

Other Components

Other agents may be incorporated into the present invention depending on the application of the material. These additives include antimicrobial and anti-inflammatories agents, initiators and coinitiators radiopacifiers, natural extracts, plastifiers, solvents, acidic monomers, hydrophobic and hydrophilic monomers, surfactants, anesthetics, among others. Examples of possible additives to bioactive dental cements are described in Table 1.

TABLE 1

Examples of possible additives in the composition

| Additive | Example |
| --- | --- |
| Radiopacifiers | Bismuth oxide, tantalum oxide, calcium tungstate, zirconia, ytterbium fluoride, glass filler particles containing barium, strontium, zinc. |
| Antimicrobial agents | Quaternary ammoniums, pyrazole derivatives, functionalized methacrylates, chlorhexidine, antimicrobial monomers (such as MDPB), Benzalkonium chloride, Cetylpyridinium chloride, Silver particles, Triclosan. |
| Natural extracts (antimicrobial, anti-inflammatory) | Essential oils of copaiba, butiá, vitis, cardol, cardenol, oregano, aroeira, garlic, propolis |
| Others | Anti-inflammatory, corticosteroid, and haemostatic agents, analgesics, anesthetics. |

EXAMPLES

In order to provide a better understanding of the present invention and to clearly demonstrate the technical advances obtained, examples of incorporation of the materials are presented below, and it is not the purpose of this report to limit the invention to these incorporations only.

Example 1: Orthodontic Cement Containing Metal-Containing Methacrylates

Table 2 exemplifies the formulation of an orthodontic cement containing metal-containing methacrylates in its composition. The cement is composed mainly of hydrophobic monomers such as Bis-GMA and TEGDMA, initiators such as camphorquinone, metal-containing methacrylates such as Copper and Silver containing Methacrylate, and others.

TABLE 2

Example of orthodontic cement containing metal-containing methacrylates in the composition

| Component | Wide range | Preferred range |
|---|---|---|
| Bis-GMA | 5-90% wt | 60-80% wt |
| TEGDMA | 2-80% wt | 15-30% wt |
| Camphorquinone | 0.1-40 mol % | 0.1-5 mol % |
| EDAB | 0.1-40 mol % | 0.1-2 mol % |
| DPIHFP | 0.1-50 mol % | 0.1-5 mol % |
| Copper Methacrylate | 0.1-60 mol % | 5-25 mol % |
| Silver Methacrylate | 0.1-70 mol % | 0.5-10 mol % |

To evaluate the example in Table 1 of the present invention, the degree of conversion (DC), water sorption (WS) and solubility (S), microshear bond strength (SBR), enamel color difference (ΔE), flexural strength, modulus of elasticity, cytotoxicity (ISO 10993; 2009), and the antimicrobial effect against strains of Streptococcus mutans through the agar diffusion test (IZ) and direct contact (DC). The enamel surface roughness (Sa), the lost enamel volume (V) after the wear of the cement remnant, and the wear time of the remaining cement on the tooth structure were also tested. As a commercial reference, Transbond XT® Orthodontic Cement (TB) and Filtek Z 250 Composite Resin ($R_{Z250}$) were used. Data were analyzed using Sigma Plot® software version 12.0 considering $p<0.05$ as statistically significant. Degree of Conversion (DC), Water Sorption (WS) and Solubility (S) in Water, and Microshear Bond Strength (SBS)

In relation to the DC, the addition of Silver Methacrylate and Copper influenced the polymerization, increasing the percentages (CMCu=49.4%, CMAg=48.3%, C=49.8%, TB=42.7% and RZ 250=37.7%). In WS, values ranged from 0.54% for TB to 4.26% for $C_{MCu}$. For S, the percentage varied between 0.16% for $C_{MAg}$ and 0.5% for C, and there was no statistical difference between them. The commercial cements tested showed the highest values (TB=24.5 and RZ250=22.6), while the experimental cements evaluated showed lower values (C=18.2 $C_{MCu}$=12.1 and $C_{MAg}$=16.5).

TABLE 3

Degree of Conversion (DC), Water Sorption (WS) and Solubility (S) and Microshear Bond Strength (SBS)

| Groups | DC (%) | WS (%) | S (%) | SBS (MPa) |
|---|---|---|---|---|
| TB | $42.7^B$ (±2.2) | $0.54^A$ (±0.2) | 0.21 (±0.3) | $24.5^A$ (±4.7) |
| $R_{Z250}$ | $37.7^A$ (±0.8) | $1.18^B$ (±0.3) | 0.22 (±0.3) | $22.6^A$ (±8.2) |
| C | $49.8^C$ (±1.2) | $3.77^{CD}$ (±0.5) | 0.50 (±0.4) | $18.2^B$ (±6.5) |
| $C_{MCu}$ | $49.4^C$ (±1.8) | $4.26^D$ (±0.7) | 0.25 (±0.6) | $12.1^C$ (±3.9) |
| $C_{MAg}$ | $48.3^C$ (±0.7) | $3.37^C$ (±0.6) | 0.16 (±0.5) | $16.5^B$ (±5.2) |

Different capital letters in the same column indicate statistically significant difference between groups. One-way ANOVA followed by the Tukey test (Mean ± Standard deviation) ($p < 0.05$).

Antimicrobial Activity Evaluation

In the agar diffusion test, the cement with copper methacrylate had the highest inhibition halo values, with a median of 14 mm, and with silver methacrylate, 8 mm (FIG. 1). The other tested cements did not present any halo. In DC, $C_{MCu}$ showed a higher antimicrobial effect in comparison with the other cements, presenting growth close to zero in a 24-hour contact period.

Cell Viability Evaluation

Figure 2:
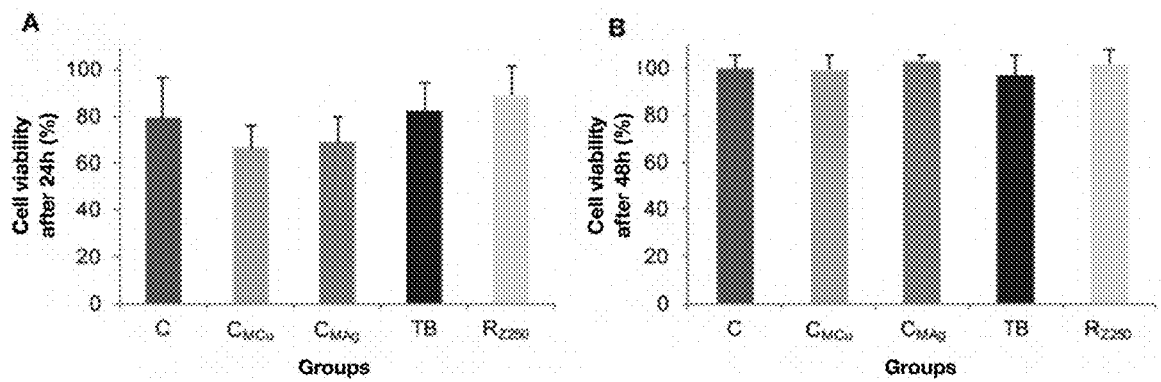
FIG. 2 shows Cell viability and standard deviation (%) of the groups tested in 24 h (A) and 48 h (B) without any statistically significant difference observed ($p>0.05$).

The cell viability assay was performed according to ISO 10993 (2009). After 24 and 48 h contact of the L929 mouse fibroblast cells with the eluate of the materials, the cytotoxicity with WST-1 was assessed (Roche, USA). All cement concentrations showed statistically similar cytotoxicity with $C_{MCu}$ exhibiting 68.6% cell viability and $C_{MAg}$ presenting 66.2% (FIG. 2). After 48 h, all groups presented cell viability higher than 96%, demonstrating that orthodontic cements containing metal-containing methacrylates were not cytotoxic.

Evaluation of the Difference in Tooth Enamel Color (ΔE)

Figure 3:
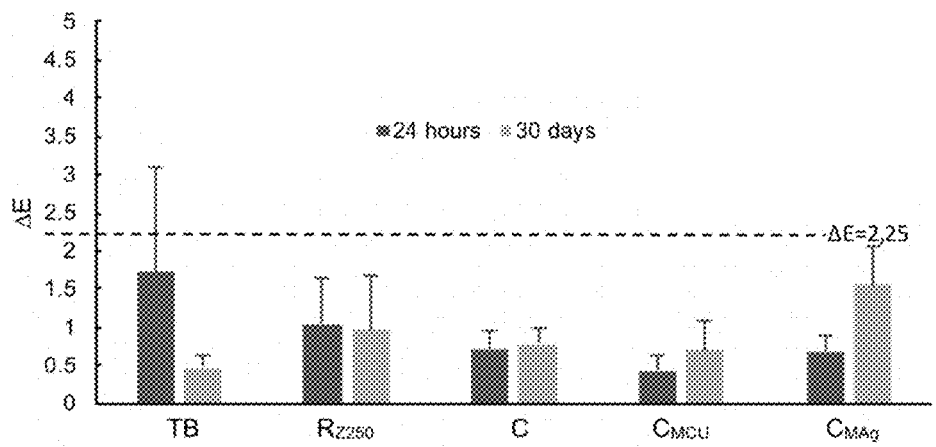
FIG. 3 shows Enamel color difference ($\Delta E$) after application of the different materials tested.

Regarding the difference in tooth enamel color (ΔE), both metallic methacrylate-containing cements and commercial cements were unable to pigment and change the enamel color. The cements presented values between TB=0.47 and $C_{MAg}$=1.55, all below the value considered perceptible to the human eye, ΔE=2.25 (FIG. 3).

Flexural Strength Test and Elasticity Modulus

For flexural strength (MPa) the values were: TB=115.9; RZ250=120.4; C=75.5, $C_{MAg}$=73.5 and $C_{MCu}$=67.1. The modulus of elasticity varied between 5544.5 to $R_{Z250}$ and 1222.7 to $C_{MCu}$.

Evaluation of Surface Roughness and Amount of Lost Enamel

After carrying out the mechanical and microbiological tests, the clinical application of these procedures was tested, by cementing orthodontic brackets to bovine enamel. The bracket cementation technique was performed according to a adhesive system application protocol (phosphoric acid and adhesive): cement applied to the bases of the accessories, accessory positioned on the enamel, under pressure to remove excess material, allowing a thin layer to remain under the accessory, and photoactivation for 20 s on each side of the bracket, totaling 80 s. The samples were stored in distilled water for 24 hours, and after this time had elapsed, the brackets were removed with bracket remover pliers.

The cement residues remaining on the enamel structure were removed with the same type of drill for all groups and the influence of the color on removal of the cement residue was evaluated. The surface roughness (Sa) and amount of enamel lost, in volume (V)-mm3, generated by the removal process were evaluated.

The enamel Sa was similar between the groups, with the following results: TB=0.107; $R_{Z250}$=0.101, C=0.096, $C_{MCu}$=0.271 and $C_{MAg}$=0.222. The V, relative to the enamel lost after the removal of the remaining cement residue was: TB=0.001024; $R_{Z250}$=0.001407, C=0.000824; $C_{MCu}$=0.001156 and $C_{MAg}$=0.001204.

As regards the time taken to remove the cement remnant, the addition of the methacrylates significantly reduced this time (TB=57.4 s, $R_{Z250}$=79 s, $C_{MCu}$=32.8 s and $C_{MAg}$=34 s).

Example 2: Endodontic Sealer Containing Metal-Containing Methacrylates

The endodontic cement containing metal-containing methacrylates can preferably be prepared by mixing methacrylate, dimethacrylates and the initiation system, such as amine/peroxide (chemical activation) and camphorquinone/amine (photopolymerization), and radiopacifiers into the inorganic matrix (Table 4 and 5). The material is composed of the base and catalyst pulps?/pastes(?). The base paste is: ethoxylated bisphenol-A glycidyl dimethacrylate (Bis-EMA30), Exothane 8, Peg400α=25 dimethacrylate and triethylene glycol dimethacrylate (TEGMA), camphorquinone, DHEPT, unsilanized silica, ytterbium. Bis-EMA 30, Exothane 8, TEGDMA, sulfinic acid?/salt?, benzoyl peroxide, BHT, non-silanized silica and ytterbium are added to the catalyst slurry.

TABLE 4

Example of endodontic sealer containing metal-containing methacrylates in the base paste composition

| Component | Wide range | Preferred range |
|---|---|---|
| Bis-EMA 30 | 1-99% | 60-80% |
| TEGDMA | 1-85% | 5-30% |
| Peg 400 | 1-50% | 10-30% |
| Camphorquinone | 0.1-30% | 0.1-5% |
| DHEPT | 0.1-30% | 0.1-3% |
| Silica | 0.1-50% | 0.1-10% |
| Radiopacifier | 0.1-60% | 15-30% |
| Dibutyltin or calcium methacrylate | 0.1-70% | 0.5-20% |

TABLE 5

Example of endodontic sealer containing metal-containing methacrylates in the catalyst paste composition

| Component | Wide range | Preferred range |
|---|---|---|
| Bis-EMA 30 | 1-99% | 50-80% |
| TEGDMA | 1-85% | 5-30% |
| Exothane 8 | 1-50% | 5-40% |
| Sulfinic acid | 0.1-35% | 0.1-5% |
| Benzoyl peroxide | 0.1-40% | 0.1-2% |
| BHT | 0.1-45% | 0.1-5% |
| Silica | 0.1-55% | 0.1-15% |
| Radiopacifier | 0-80% | 5-40% |

To evaluate the endodontic sealer developed, the film thickness, the degree of conversion (DC), radiopacity, the antimicrobial effect against strains of *Enterococcus faecalis* ATCC4083, and cytotoxicity were analyzed, using the modified direct contact test (MDCT). RealSeal® (RS) was used as commercial reference. Data were analyzed using Sigma Plot® software version 12.0. Basically the data were analyzed with two-way ANOVA followed by the Tukey complementary tests for the parametric, and SNK tests, for the non-parametric tests ($\alpha < 5\%$).

Evaluation of Degree of Conversion (DC)

For DC, the experimental sealer with photo/chemical polymerization was influenced by the addition of metallic methacrylates, causing an increase in DC percentage, results shown in Tables 6 and 7.

TABLE 6

Degree of conversion (DC). Radiopacity (R). Film thickness (PE) of the different materials containing calcium methacrylate (mean ± standard deviation).

| Group | GC (%) | R (mm Al) | FT (μ) |
|---|---|---|---|
| C | 22 ± 7 | 2.5 ± 0.2b | 19 ± 6c |
| Ca 0.5% | 37 ± 3 | 2 ± 0.4b | 19 ± 1c |
| Ca 1% | 52 ± 11 | 2 ± 0.2b | 32 ± 5bc |
| Ca 2% | 60 ± 11 | 2.3 ± 0.2b | 26 ± 10bc |
| Ca 5% | 45 ± 1 | 2.4 ± 0.5b | 38 ± 9ab |
| RS | 5 ± 1 | 7.5 ± 0.2$^a$ | 23 ± 3bc |

Different letters present statistically significant difference between groups ($p < 0.05$). Cements containing calcium methacrylate at different concentrations (Ca); RealSeal® (RS). C without metal-containing methacrylates (Control).

Evaluation of Film Thickness (FT)

With respect to determining the FT, the addition of Sn and Ca increased the film thickness value in comparison with the experimental sealer without the addition of metallic methacrylates, ranging from 22 μm to 38 μm. These values are in accordance with ISO 6876 (2001).

Evaluation of Radiopacity (R)

Regarding the radiopacity, the addition of metal-containing methacrylates to the experimental sealer showed no change in radiopacity, and Real Seal was the most radiopaque of all the cements evaluated.

Evaluation of the Antimicrobial Activity by Modified Direct Contact Test (TDCT)

Sealer with 5% Ca addition in TDCT showed a higher antimicrobial effect when compared with the other methacrylate concentrations, after 24 h it showed the highest effect. While for dibutyl tin, 0.5% Sn had a higher antimicrobial effect compared with the other cements containing this same monomer, and the best period for this effect was after 48 hours.

Evaluation of Cell Viability

Figure 4:
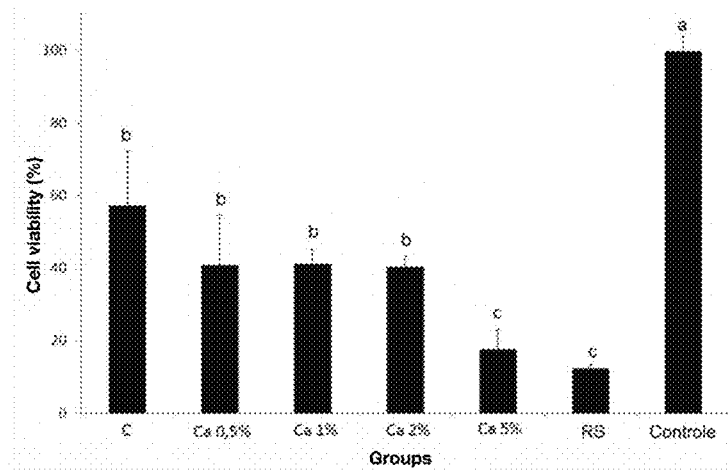
FIG. 4 shows Cell viability (%) of L929 fibroblasts after exposure to the experimental cement with calcium methacrylate (Ca). Results are expressed as mean and standard deviation (SD) according to the control of cells (untreated group), which was considered 100%. ES did not contain metal-containing methacrylates (Control). Different letters indicate statistically significant difference ($p<0.05$).
Figure 5:
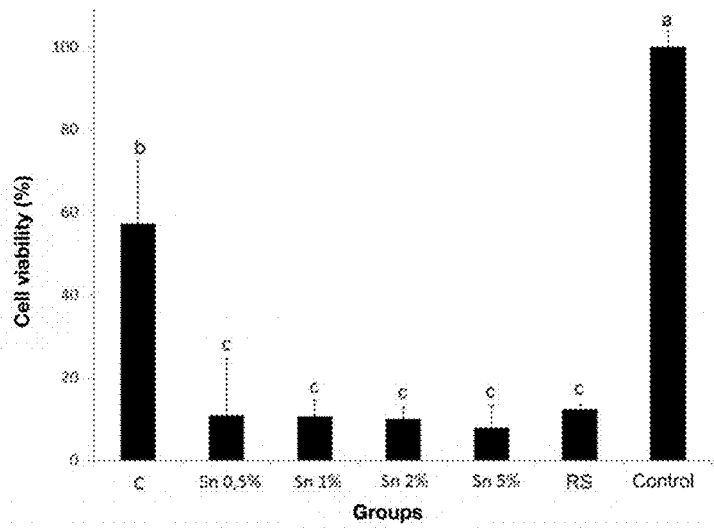
FIG. 5 shows Cell viability (%) of L929 fibroblasts after exposure to the experimental cement with dibutyltin methacrylate (Sn). Results are expressed as mean and standard deviation (SD) according to the control of cells (untreated group), which was considered 100%. Different letters indicate statistically significant difference ($p<0.05$).

In cytotoxicity assays, all concentrations of Sn were statistically similar to RS, with cell viability of 12% (FIG. 4). Ca 0.5% presented cell viability of 42%, and Ca 5% was statistically similar to RS ($p<0.001$) (FIG. 5). The incorporation of metal-containing methacrylates into the material, depending on the concentration and type of methacrylate, showed an antimicrobial effect and biocompatibility without altering the physicochemical properties of the sealers tested.

Example 3: Resins/Sealants Containing Metal-Containing Methacrylates

The resin/sealant containing metal-containing methacrylates may preferably be prepared by mixing methacrylate, trimethacrylates, acid monomer, solvent, initiation and photopolymerization system, and charge particle. The material is self-adhesive and the following were added: bisphenol-A glycidyl methacrylate (Bis-GMA), trimethylolpropane trimethacrylate (TMPTMA), glycerol dimethacrylate phosphate (it is an equimolar mixture of glycerol dihydrogen phosphate glycerol dimethacrylate and phosphate tetramethacrylate Hydrogen-GDMA-P); Phenylbis(2,4,6-trimethylbenzoyl)phosphine oxide (BAPO); Diphenyliodonium hexafluorophosphate (DPIHFP). A possible sealant composition is exemplified in Table 7. To evaluate the self-adhesive sealant developed, depth of cure and flexural strength were analyzed.

TABLE 7

Example of sealant containing metal-containing methacrylates in the composition

| Component | Wide range | Preferred range |
|---|---|---|
| Bis-GMA | 1-99% | 5-25% |
| TMPTMA | 1-85% | 15-35% |
| GDMA-P | 20-70% | 30-45% |
| Water | 0.1-30% | 0.1-6% |
| BAPO | 0.1-30% | 0.1-10% |
| DPIHFP | 0.1-50% | 0.1-5% |
| Silica nano aerosil | 0.1-60% | 5-25% |
| Dibutyltin methacrylate | 0.1-70% | 0.1-20% |

Flexural Strength

Specimens with dimensions of 12 mm×2 mm×2 mm were made from each sealant (n=10) by using a mold. All specimens were submitted to a three-point bending test in a universal test machine, EMIC (DL-500, Emic, Sao Jose dos Pinhais, Brazil) at a speed of 1 mm/min. The flexural strength test was calculated in MPa. The addition of 1% tin methacrylate did not affect the tensile strength and modulus of elasticity of the material (Table 8).

Depth of Cure

Discs were made with the sealants by using a mold measuring 6 mm thick and 4 mm in diameter. The disc thickness of the polymerized material was measured with a micrometer to an accuracy of 0.1 mm. Three determinations were performed and all could not be less than 1.5 mm (ISO 6874, 2005). The addition of 1% tin methacrylate did not affect the curing depth of the material (Table 8).

TABLE 8

Flexural Strength and depth of cure of the different materials containing dibutyltin methacrylate (Mean ± Standard Deviation)

| Group | Flexural Strength | Young's modulus | Polymerization Depth |
|---|---|---|---|
| Control | 39.2 (±9.6) | 1209.5 (±240.9) | 5.88 (±0.14) |
| Sn 1% | 40.5 (±10.3) | 1309 (±235.1) | 5.7 (±0.1) |

The present examples serve as proof of the concept of potential application and effect of materials containing metal-containing methacrylates for use in dentistry. It should be understood that the preferred embodiments mentioned here are merely illustrative of the present invention. Numerous variations in design and use of the present invention may be contemplated in view of the following claims without straying from the intended scope and field of the invention herein disclosed.

The invention claimed is:

1. A dental cement comprising a monomeric antimicrobial polymerizable composition containing greater than 1% and up to 30% by weight of at least one metal-containing methacrylate, selected from the group consisting of: tin, iron, nickel, and combinations thereof, incorporated into a curable organic matrix with low level of leachability containing at least one type of inorganic filler, a radiopacifier, a polymerization initiation system, an inhibitor of polymerization and optical modifiers.

2. A monomeric antimicrobial polymerizable dental composition comprising the at least one metal-containing methacrylate according to claim 1, having an inorganic/organic ratio designed to provide a high viscosity restorative composite material.

3. A monomeric blend adhesive composition containing the at least one metal-containing methacrylate according to claim 1, to provide dental material with radiopacity.

4. A monomeric antimicrobial polymerizable dental composition comprising the at least one metal-containing methacrylate according to claim 1, with viscosity adjustments to provide a flowable composite for use as a dental cement in an orthodontic or endodontic treatment.

5. An antimicrobial polymeric composition containing the at least one metal-containing methacrylate according to claim 1, containing monomers in the composition to render the material self-activated, photoactivated, chemically activated or dual-cure activated.

6. An antimicrobial polymeric composition comprising the at least one metal-containing methacrylates according to claim 1, further comprising radiopacifiers in the composition, selected from the group consisting of: bismuth oxide, tantalum oxide, calcium, zirconia tungsten, ytterbium fluoride, barium, strontium, zinc containing glass filler particles; and combinations thereof.

7. An antimicrobial polymeric compositions composition containing the at least one metal-containing methacrylates according to claim 1, further comprising additives in compositions selected from the group consisting of: anti-inflammatory agents, antimicrobial agents, antiviral agents, corticosteroids, hemostatic agents, analgesic agents, anesthetic agents and combinations thereof.

8. An antimicrobial polymeric composition containing the at least one metal-containing methacrylates according to claim 1, further comprising additional antimicrobial or antiviral agents selected from the group consisting of: quaternary ammoniums; functionalized pyrazole; methacrylate derivatives selected from the group consisting of: tin; chlorhexidine; MDPB (12-methacryloyloxy dodecypyridinium bromide); and combinations thereof.

9. An antimicrobial polymeric composition comprising the at least one metal-containing methacrylates according to claim 1, and further comprising natural extracts in compositions selected from the group consisting of: copaiba, butyral, vitis, cardol, cardenol essential oils, oregano, aroeira, garlic, propolis, and combinations thereof; for polymer plasticizers.

10. A dental cement comprising a monomeric antimicrobial polymerizable composition containing greater than 0.1% and up to 30% by weight of at least one metal-containing methacrylate, selected from the group consisting of: tin, iron, nickel, and combinations thereof, incorporated into a curable organic matrix with low level of leachability containing at least one type of inorganic filler, a radiopacifier, a polymerization initiation system, an inhibitor of polymerization and optical modifiers.

11. A monomeric antimicrobial polymerizable dental composition comprising the at least one metal-containing methacrylate according to claim 10, with viscosity adjustments to provide a flowable composite for use as a dental cement in an orthodontic or endodontic treatment.

* * * * *